United States Patent [19]

Atebara et al.

[11] Patent Number: 4,955,904
[45] Date of Patent: Sep. 11, 1990

[54] MASKED INTRAOCULAR LENS AND METHOD FOR TREATING A PATIENT WITH CATARACTS

[75] Inventors: Neal Atebara, Boston; David Miller, Brookline, both of Mass.

[73] Assignee: The Beth Israel Hospital Association, Boston, Mass.

[21] Appl. No.: 396,558

[22] Filed: Aug. 21, 1989

[51] Int. Cl.⁵ ............................................. A61F 2/16
[52] U.S. Cl. ...................................................... 623/6
[58] Field of Search ........................................... 623/6

[56] References Cited

U.S. PATENT DOCUMENTS

| | | | |
|---|---|---|---|
| 4,409,641 | 10/1983 | Levy | 623/6 |
| 4,605,409 | 8/1986 | Kelman | 623/6 |
| 4,636,211 | 1/1987 | Nielsen et al. | 623/6 |
| 4,676,791 | 6/1987 | LeMaster et al. | 623/6 |
| 4,813,955 | 3/1989 | Achatz et al. | 623/6 |

OTHER PUBLICATIONS

"Implants With Coloured and Opaque Portions: Implants with Built-In Stenopaeic Aperture", *Intra-Ocular Lenses and Implants*, by Choyce (Book) H. K. Lewis, London, 1964, 623-6, pp. 21-26.
Miller et al., *Ann. Ophthalmol.*, (1986) 18:212-215.
Miller and Johnson, *Perspectives in Refraction*, Rubin, ed., (1977) 21:347-350.
Phillips et al., *J. Cataract Refract Surg*, (1988) 14:129-135.
Apple et al., *J. Cataract refract Surg*, (1986) 12:358-362.
Park et al., *J. Cataract Refract Surg.*, (1986) 12:363-366.
De Carle, *Review of Contact Lenses*, Ruben, ed., pp. 571-591.

*Primary Examiner*—Ronald Frinks
*Attorney, Agent, or Firm*—Lorusso & Loud

[57] ABSTRACT

A masked intraocular lens for implantation into a human eye is presented. The mask, which blocks only part of the lens body, together with the pupil of the eye, defines a small aperture in the eye when the pupil is constricted, thereby increasing the depth of focus, as a pinhole camera does. When the pupil of the eye is dilated, additional light is allowed to pass through the pupil around the mask and to reach the retina to allow a person to see in dimmer light conditions. In one embodiment, the mask defines a small circular aperture and a larger exterior annulus; the small circular aperture has an additional power intermediate between that needed for distance and close vision. Also provided is a method for treating a patient with cataracts comprising replacing the patient's lens with the lens of the invention.

15 Claims, 13 Drawing Sheets

PRIOR ART

FIG. 17

MASKED INTRAOCULAR LENS AND METHOD FOR TREATING A PATIENT WITH CATARACTS

BACKGROUND OF THE INVENTION

This invention relates to an intraocular lens for the human eye, and, more particularly, to a masked intraocular lens of the type which can be positioned in the anterior chamber, the posterior chamber, or partially in either the anterior or posterior chamber of the eye. The invention also relates generally to postcataract patient care and vision improvement by implanting a masked intraocular lens to replace the removed natural lens.

As a person ages, occasionally a person's eye lens gets cloudy. When this occurs, a person is said to have cataracts. The cataracts eventually cloud the lens so that a person cannot see clearly. When this happens, removal of the lens is required. Commonly, thick glasses have been used for correcting the vision of postcataract patients. However, the glasses have obvious disadvantages associated with the size and weight of the glasses. An intraocular lens (IOL) may be implanted to replace the human lens; however, these lenses generally are only in focus at one focal distance. The present invention circumvents the need for a traditional IOL augmented by bifocal or trifocal spectacles by implanting an intraocular lens which can focus continuously from near to far and in most light conditions.

Attempts to produce an intraocular lens that is focusable at both near and far distances have not been completely successful. In the normal eye the crystalline lens is self-biased toward a spherical shape, that is, toward maximum refraction; for example, for distance viewing it is radially tensioned, and thereby flattened, by relaxation of the ciliary body. However, once the lens is removed, a replacement lens cannot function in this manner. Thus, intraocular lenses that allow the patient near and far focusability must work on a different principle.

In U.S. Pat. No. 4,409,691, entitled "Focussable Intraocular Lens", an intraocular lens that achieves accommodation in response to contraction and relaxation of the ciliary body is disclosed. This lens works on the same principle as a lens in a camera. It achieves adjustment of the focal distance by adjustment of the spacing between the lens and the fovea. The intraocular lens is spring biased towards its distance focus position where it remains so long as the ciliary body remains relaxed. When the ciliary body contracts, it compresses the spring bias, moving the lens away from the fovea to provide accommodation for near viewing. This lens has not been completely successful as it requires precise implantation into the eye. Furthermore, implantation of this device is a more complex procedure than implantation of standard intraocular lenses. In addition, such a lens requires precise quantification of ciliary muscle body power. However, the capability of ciliary muscle is unknown, especially for elderly patients.

A second technique to try to achieve focusing for near and far vision in an intraocular lens implant is disclosed in U.S. Pat. No. 4,636,211, entitled "Bifocal Intra-ocular Lens". This patent discloses an intraocular lens that focuses for near vision in the central portion of the lens and focuses for far vision by a coaxial ring around the central portion. This lens is not completely successful as, when one focuses on a near object, it is slightly fuzzy around the edges due to the far vision coaxial ring. This creates fuzziness for the viewer.

U.S. Pat. No. 4,605,409 entitled "Intraocular Lens With Miniature Optic Having Expandable and Contractible Glare-Reducing Means", teaches an IOL with masking means for reducing the glare associated with an intraocular lens of small dimension. The masking means of that invention does not overcome the problem associated with standard IOLs, that is, it does not improve focusability.

Pinholes have been used in pinhole cameras to bring distant objects, near objects, and everything in between into continuous focus. Pinholes are used by ophthalmologists to assess retinal function; the pinhole acts as a sort of universal lens, correcting all refractive errors, including astigmatism and spherical aberration. Although it has been known that the pinhole acts in this useful way, pinhole contact lenses and pinhole IOLs (such as is described in Choyce, *Intra-Ocular Lenses and Implants*, London. H.K. Lewis, 1964. pp. 21–26) made in the past did not work in dim light conditions. In adequate light the pinhole contact lenses and the pinhole IOLs functioned as expected, allowing the patient to see in the distance as well as read a book. However, in dim light, where the pinhole fails to admit enough light into the eye, image quality declined. Essentially it was like wearing dark glasses indoors.

An earlier study of pinholes indicated that pinholes might be useful for solving vision problems caused by refractive errors if the problem of vision in dim light could be overcome. (Miller et al., "A Crossed Polaroid-Pinhole Device," *Ann. Opthalmol.*, 1986, Vol. 18, 212-15. That study also indicated that a pinhole diameter of 1.6–1.8 would provide better than 20/40 vision even in the face of artificially induced refractive errors of up to 3 diopters. Miller and Johnson also studied the pinhole effect with the hope of solving vision problems. (Miller and Johnson, "Quantification of the Pinhole Effect," in "Perspectives in Refraction," Rubin, ed., *Survey of Opthalmology*, 1977, Vol. 21, 347–50.) They found that pinholes were useful for overcoming artificially induced refractive errors, and, in particular, that pinholes with a 1.0–2.0 mm diameter were most useful. They revealed a soft contact lens which was dyed black except for a 1.5 mm aperture and which maintained 20/40 vision even in the face of a 6 diopter error, but which constricted peripheral vision. They also revealed a soft contact lens with a clear 1.5 mm pinhole defined by a blackened annulus with an outer diameter of 4.5 mm which was surrounded by an outer clear ring to improve peripheral vision. The present invention takes advantage of the focusing power of the pinhole while at the same time getting around the problem of dim illumination in low ambient light conditions.

SUMMARY OF THE INVENTION

The present invention is a masked intraocular lens (IOL) that keeps most of the world in focus in most light conditions. In normal light conditions the pupil of the eye is approximately 4 mm in diameter. The masked IOL further reduces the opening available for light to pass to the retina to approximately 1-3 mm, so that all the light that reaches the retina comes through a 1-3 mm pinhole. At this point the eye is working like a pinhole camera and there is a sharp image on the retina for near, intermediate, and far objects. In lower ambient light conditions, the pupil of the eye dilates. This dilation increases the area through which light may pass and reach the IOL. The masking on the IOL is configured so that, in turn, more of this available light may reach the retina by passing around the edges of the mask on the IOL. At this point, the eye is no longer working as a pinhole camera, but the masked IOL allows enough light to reach the retina so that an image is maintained thereon, albeit somewhat blurry. In an important embodiment of the present invention, the IOL is manufactured with an intermediate added power in the center of the IOL. This added power moves the range of depth of focus from infinity to a close distance while maintaining a high contrast image.

An object of the present invention is to provide a masked intraocular lens for postcataract patients which eliminates the need for heavy, uncomfortable glasses, or a contact lens or an IOL and reading glasses or bifocals.

Another object of the present invention is to provide the postcataract patient with an intraocular lens which enables the patient to achieve near, intermediate, and far vision with clarity.

Still another object of the present invention is to provide a pinhole intraocular lens that allows enough light to reach the retina in low ambient light conditions.

A further object of the present invention is to provide an improved method for treating a cataract patient whose natural lens must be removed without requiring the patient to wear heavy glasses and without causing significant loss of vision as compared to a normal person.

These and other features and objects of the present invention will be more fully understood through the following detailed description in which corresponding reference numerals represent corresponding parts throughout the several views.

DESCRIPTION OF THE PREFERRED EMBODIMENT

At the outset, the invention is described in its broadest overall aspects with a more detailed description following. In its broadest overall aspects, the intraocular lens of the present invention operates on a principle similar to the focusing arrangement of a pinhole camera. In a pinhole camera the aperture is small enough so that only a thin bundle of light rays, i.e., a small blur circle, passes through the pinhole to ultimately produce a sharp image on the film. By properly masking the intraocular lens implant all the light entering the eye is in a thin bundle, which is perceived as a sharp image by the retina; therefore, more of the world is in focus. This effect works well when there is plenty of light; however, when there is little ambient light a pinhole does not allow enough light to reach the retina. The IOL of the present invention is masked in some areas by black opaque material. In bright light the pupil constricts, and the mask allows only a pinhole of light into the eye.

The pinhole defined by the mask has a diameter of 1-3 mm. This forms a sharp pinhole image on the retina. In dim light, the pupil dilates. When the pupil is dilated, light can pass through the pupil and the pinhole in the IOL, but also around the edges of the mask away from the pinhole increasing the number of light rays which reach the retina. Thus, a greater percentage of available light enters the eye in low light conditions allowing a person to see.

In one important embodiment, the area of the IOL defined by the mask as a pinhole has an added power. In this embodiment, the dioptic power of the central IOL region (diameter between 1-3 mm) is slightly higher (0.5 to 2.5 diopters higher) than the base IOL power. This added power is not as strong as bifocal IOLs now being tested which have powers to approximately 3 diopters. Yet, this "intermediate add" helps the pinhole focus up close while at the same it does not produce the decrease in contrast seen with higher power adds. Also this intermediate add does not disturb distance vision when the pupil is constricted around the add in bright light conditions. The power of the lens peripheral to the opaque mask is that needed for distance vision. Thus, the lens can have two powers (intermediate and distance), separated by an opaque area.

Figure 1:
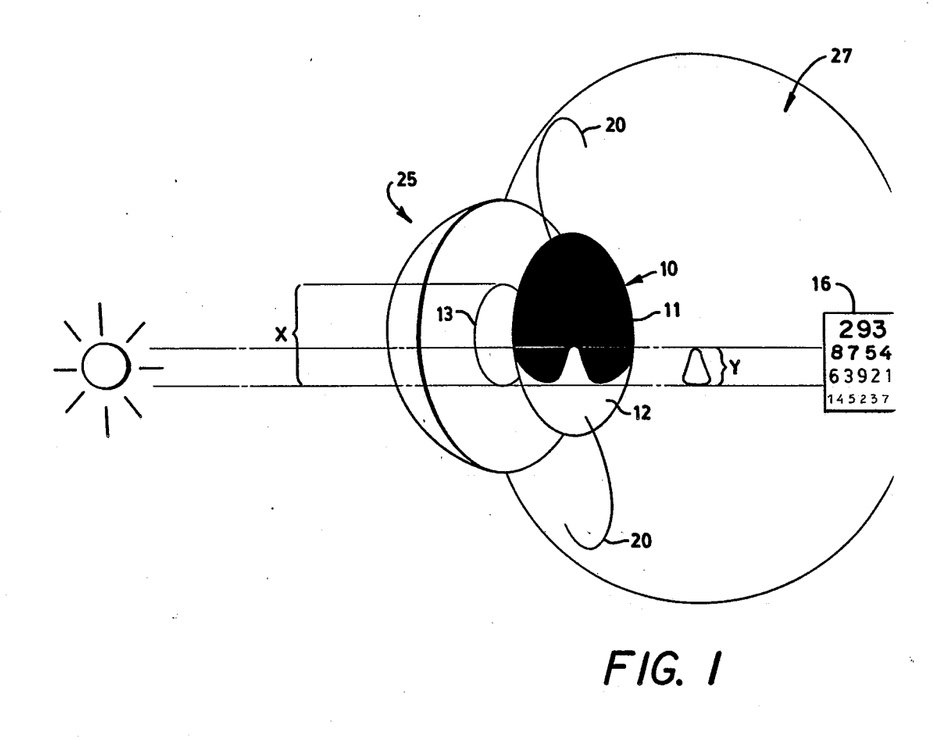
FIG. 1 shows a schematic view of an eye with an implanted IOL which represents one embodiment of the present invention, an its optical relationship with the pupil in high light conditions.

Referring to FIG. 1, the masked intraocular lens is indicated generally by 10. The mask is indicated by 11. The transparent part of the lens 10 is indicated by 12. As can be seen from FIG. 1, the pupil 13 of the eye 25 has constricted so that there is an approximately 4-4.5 mm diameter opening x which allows light through the eye 25 to the retina 18. The masking 11 of the intraocular lens 10 reduces this 4–4.5 mm diameter x to approximately 1–3 mm as is shown by bracket y. The eye 25 in this situation acts as a pinhole camera, and the image 16 on the retina 18 is sharp for near objects, far objects, and everything in between.

Figure 2:
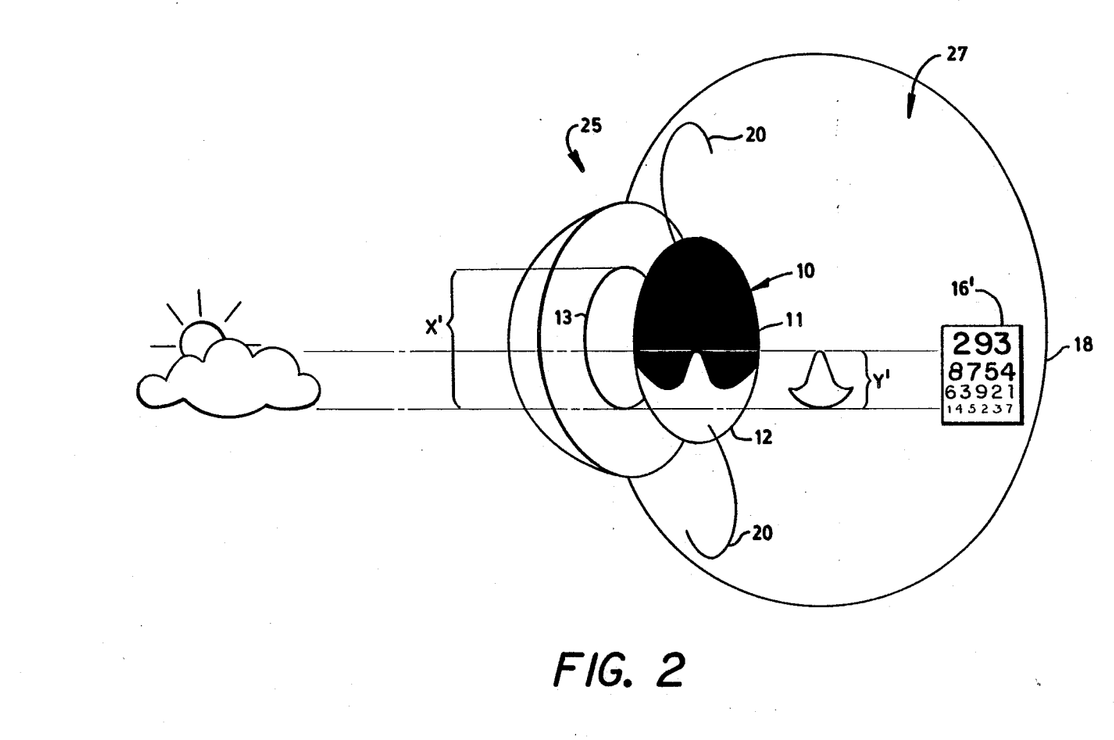
FIG. 2 shows a schematic view of an eye with an implanted IOL of FIG. 1 of the present invention, and its optical relationship with the pupil in low light conditions.

Shown in FIG. 2 is a schematic drawing of the eye 25 with the implanted intraocular lens 10 of the present invention and the optics of the eye and IOL lens in low light conditions. Here, the pupil 13 has dilated to approximately 5–7 mm (x') in diameter due to the low light conditions. With this dilation, the pupil 13 allows much more light to reach the IOL 10 and allows light to reach the unmasked portion 12. The diameter of the area of the transparent portion 12 of the IOL 10 through which light passes is now the enlarged diameter represented by the bracket y' in FIG. 2. Thus, more rays of light reach the retina 18. The eye 25 in this situation no longer acts as a pinhole camera, but the intraocular lens 10 allows enough light to reach the retina 18 so that an image 16 is maintained although it may be slightly blurry.

Figure 3:
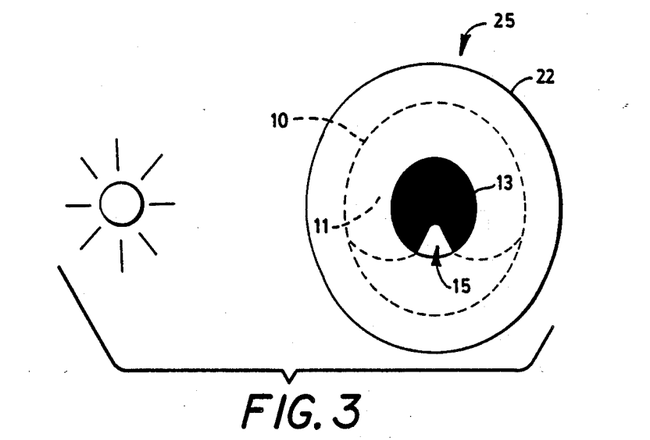
FIG. 3 shows a frontal view of an eye with an implanted IOL of FIG. 1 as it would appear to a viewer in high light conditions.
Figure 4:
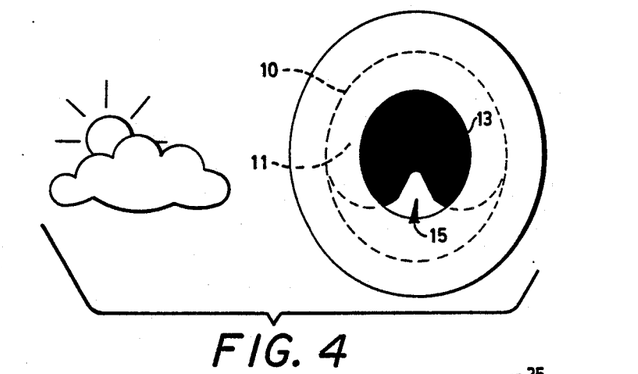
FIG. 4 is a view similar to FIG. 3 but shows how the eye would appear to a viewer in moderate light conditions.
Figure 5:
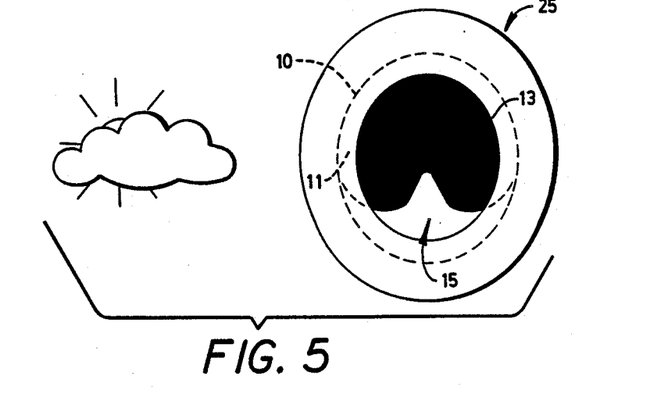
FIG. 5 is a view similar to FIG. 3 but shows how the eye would appear to a viewer in low light conditions.

Referring to FIGS. 3 to 5, frontal views of the eye 25 are shown with the implanted intraocular lens 10. FIG. 3 shows the IOL 10 in the eye 25 as it would appear to a viewer in high light conditions. The contracted pupil 13 and the mask 11 of the IOL 10 function together to define a pinhole aperture 15. At this point the eye 25 is functioning as a pinhole camera. In FIG. 4, the ambient light has been reduced and the pupil 13 has dilated to compensate for this light reduction. The aperture 15 created by the opening in the pupil 13 and the masked IOL 10 is larger than in high light conditions. The eye 25 in this condition is still functioning as a partial pinhole camera although there may be some fuzziness in the image (not shown) received. In FIG. 5, the pupil 13 is fully dilated due to the low light condition and the aperture 15 is very much expanded. The eye 25 in this case is no longer functioning as a pinhole camera and enough light is allowed through the mask 11 to allow a person to see. The area of the IOL through which light may pass when the pupil is fully dilated is larger than the area of the IOL through which light may pass when the pupil is constricted.

In the preferred embodiment of the invention, it is envisioned that the masked IOL 10 will be inserted in the posterior chamber 27 of the eye 25. Currently this type of intraocular lens implantation technique is the most common in the United States. Shown in FIGS. 1 and 2 is a schematic view of the masked intraocular lens 10 containing J-loops 20. It is also envisioned that the intraocular lens 10 of the present invention can be manufactured with C-loops or circular loops. The IOL of the present invention preferably includes a means for attachment to the eye. However, a particular means for attachment forms no part of the invention. It is envisioned that the masked intraocular lens 10 will be implanted by "in the bag" fixation. Further, "in the bag" or ciliary sulcus fixation can be used for posterior chamber lens fixation. Of course, the method used to implant the IOL of the present invention forms no part of the invention.

Figure 6:
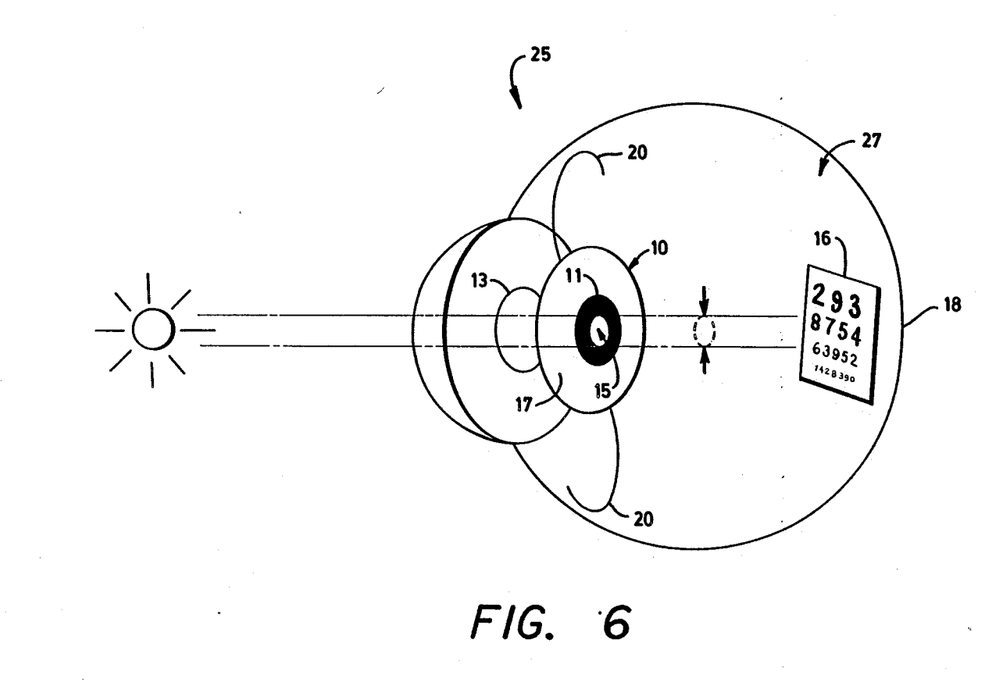
FIG. 6 shows a schematic view of an eye and a second embodiment of the masked IOL of the present invention, and its optical relationship with the pupil in high light conditions.
Figure 7:
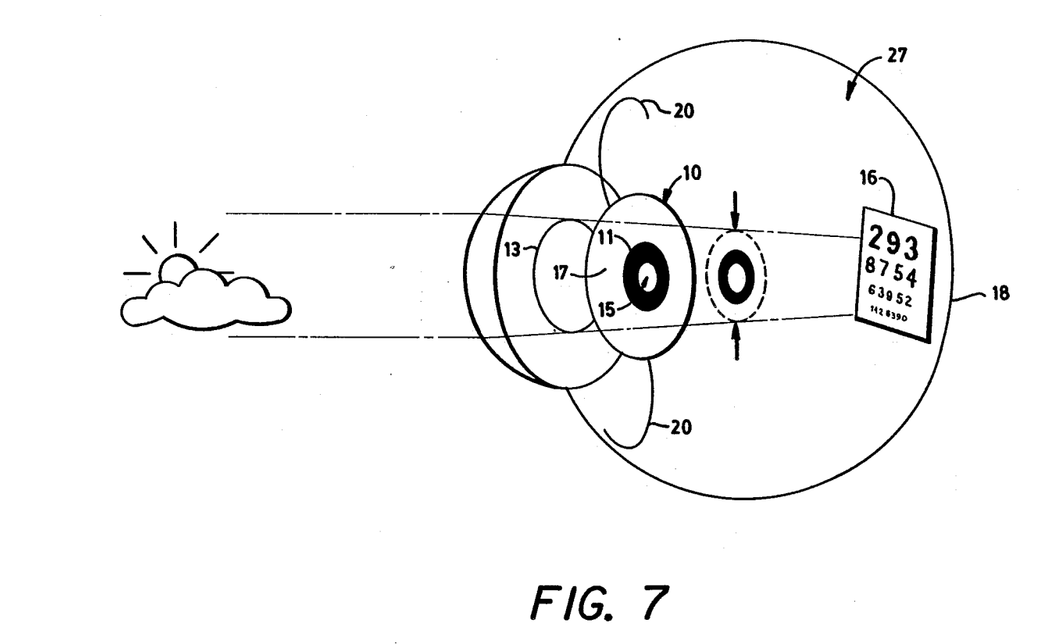
FIG. 7 shows a schematic view of an eye and the second embodiment of the masked IOL of the present invention, and its optical relationship with the pupil in low light conditions.

Shown in FIGS. 6 and 7 is a second embodiment of the masked IOL 10 of the present invention. In FIGS. 6 and 7, part of the lens 10 is blocked off by an opaque annular black mask 11. In bright light, the pupil constricts so that only light within the area of the mask can pass through with the mask 11 allowing only a pinhole of light to pass through the IOL 10, thus forming a sharp image 16 on the retina 18. In FIG. 7, in dim light conditions, the pupil 13 dilates, and light enters the eye 25, not only through the pinhole 15, but also from the circular clear area 17 surrounding the opaque annulus 11. This results in an enlarged aperture that maintains the amount of light entering the eye. Pinhole research (Miller et al., supra) has shown that a 1.8 mm pinhole maximally accomplishes continuous focusability from reading distances all the way out to infinity, equivalent to an accommodation of three diopters. However, for the lens of the present invention, the preferred pinhole is 1–3 mm in diameter, not just 1.8 mm. The preferred outside diameter of the opaque annulus 11 is 4–6 mm. The preferred width of the opaque annulus is approximately 1.5 mm. The area of the opaque annulus is larger than the area of the pinhole. The preferred configurations are shown in Table 1 below.

TABLE 1

| Pinhole Diameter | Width of Pinhole Plus Masked Annulus | IOL Diameter |
| --- | --- | --- |
| 1 mm | 4 mm | 6-7 mm |
| 2 mm | 5 mm | 6-7 mm |
| 3 mm | 6 mm | 7 mm |

Figure 8:
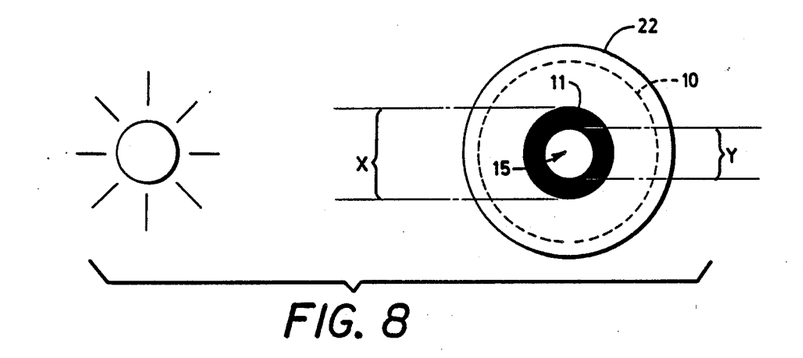
FIG. 8 shows a frontal view of an eye with an implanted IOL of FIG. 6 as it would appear to a viewer in high light conditions.
Figure 9:
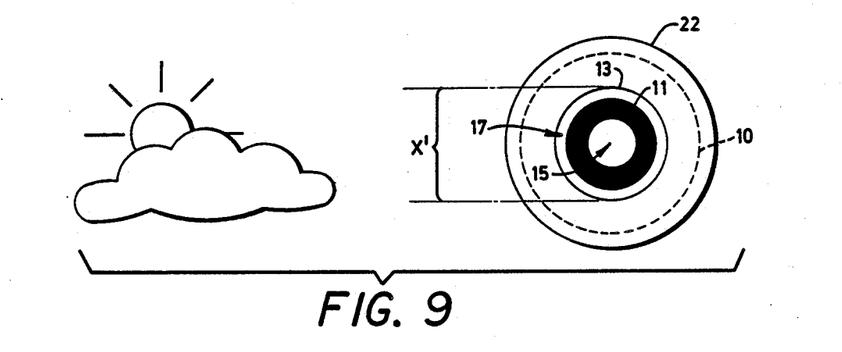
FIG. 9 is a view similar to FIG. 8 but shows how the eye would appear to a viewer in moderate light conditions.
Figure 10:
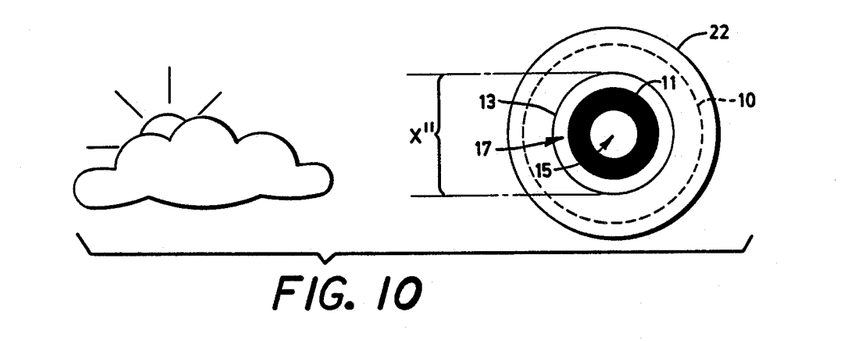
FIG. 10 is a view similar to FIG. 8 but shows how the eye would appear to a viewer in low light conditions.

Shown in FIGS. 8, 9, and 10 are front views of an eye with one embodiment of the masked IOL 10 of the present invention implanted as it would appear to a viewer. FIG. 8 shows the eye in bright light conditions where the pupil 13 has constricted to a diameter x of approximately 3.5 mm around the mask 11 of the IOL 10 such that only a pinhole of light is allowed through the IOL 10. The pinhole diameter y, may be 1–3 mm. In FIG. 9 the ambient light has decreased to moderate conditions and the pupil 13 of the eye is dilated to a diameter x' of approximately 4.5 mm so that light is let in through the pupil 13 and past the clear region 17 between the outer edge of the annulus 11 and a remainder of the IOL not blocked by the pupil 13. Of course, light also passes through the center of the masked IOL 10 on to the retina. The area of the aperture through which light passes is that of a circle having a diameter of 4.5 mm minus the area of the annulus 11. In FIG. 10, where ambient light has decreased further, the pupil has dilated even more to a diameter x" of approximately 5.6 mm, thus allowing a bigger ring of light to pass through the clear region 17. The area of the aperture through which light passes is that of a circle with a diameter of 5.6 mm minus the area of the annulus 11. In the drawings, the iris is indicated by 22.

In order to compensate for the slight pinhole enlargement over 1.8 mm, the lens power of the central region may be enhanced slightly, by 0.5–2.5 diopters. This intermediate add helps the pinhole to focus from far away to up close, while at the same time not producing the decrease in contrast seen in the bifocal IOLs with approximately 3.0 diopter adds now being tested. In addition, by not using a full 3.0 diopter add, the patient can see far distances with a constricted pupil on a sunny day.

Figure 11:
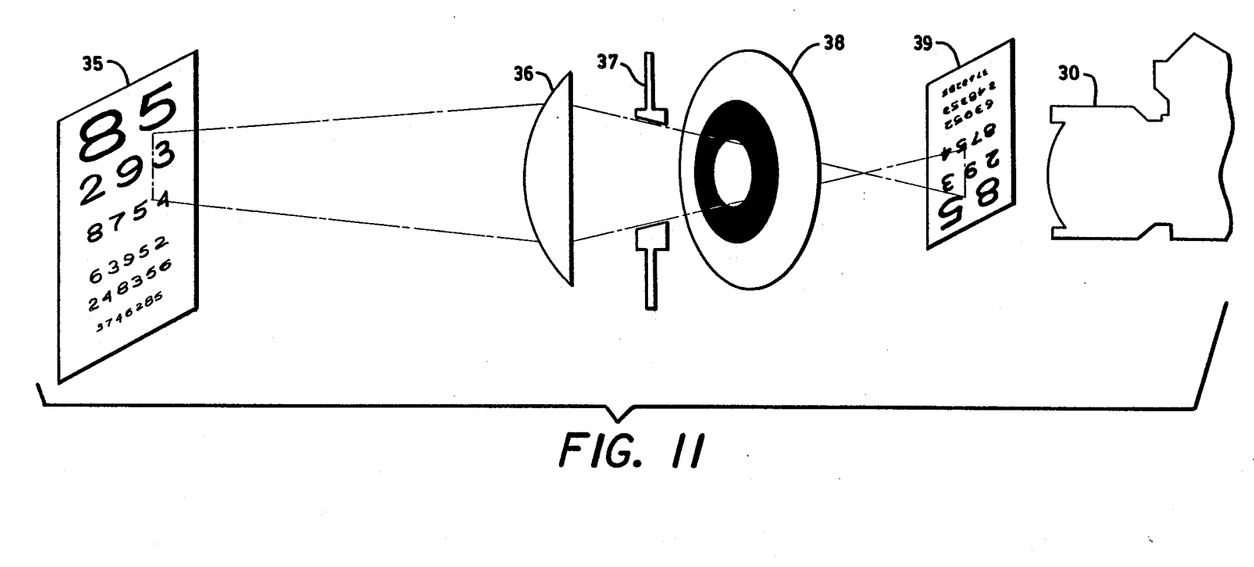
FIG. 11 shows an experimental setup for testing the masked IOL of the present invention.

Shown in FIG. 11 is a model eye for conducting experiments to determine the effectiveness of the masked IOL of the present invention. A model eye was constructed as shown in FIG. 11. In this figure, an illuminated Snellen Chart 35 is shown which represents the outside world at reading distance. Also shown is a model cornea 36, a model pupil 37 and a model masked IOL 38. The cornea is simulated with an appropriately powered spherical convex lens 36 as is the masked IOL 38. The pupil is simulated with a variable aperture 37 and the retina is simulated by a screen 39 upon which an image is projected. This "retinal" image was photographed using a non-contrast enhancing film by the camera 30.

Figure 12:
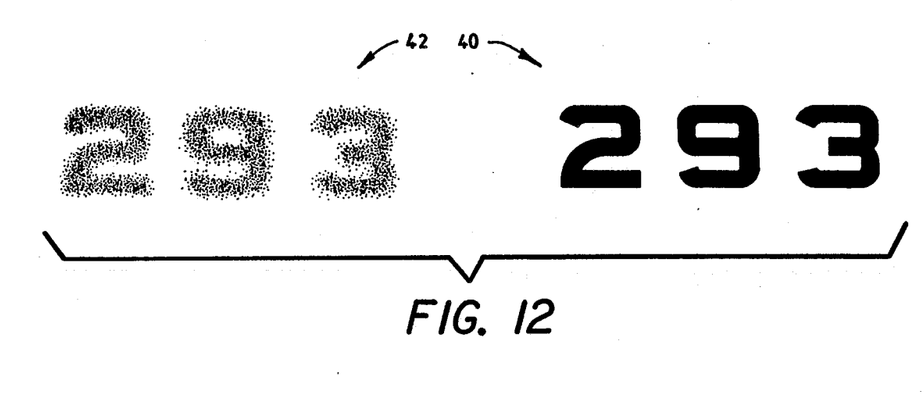
FIG. 12 shows a comparison of the masked IOL and a standard IOL for reading distance images.
Figure 13:
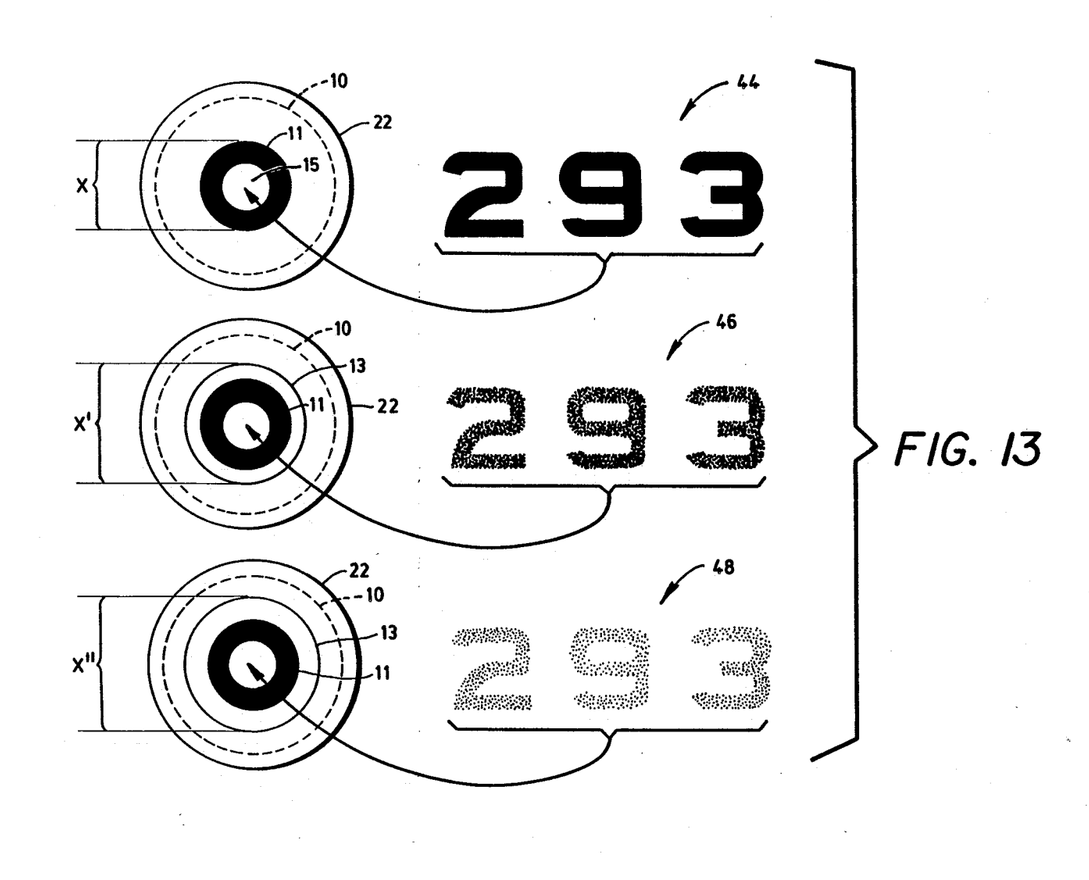
FIG. 13 shows the results of a test comparing pupil size and vision clarity using the masked IOL of the present invention with different pupil sizes.
Figure 14:
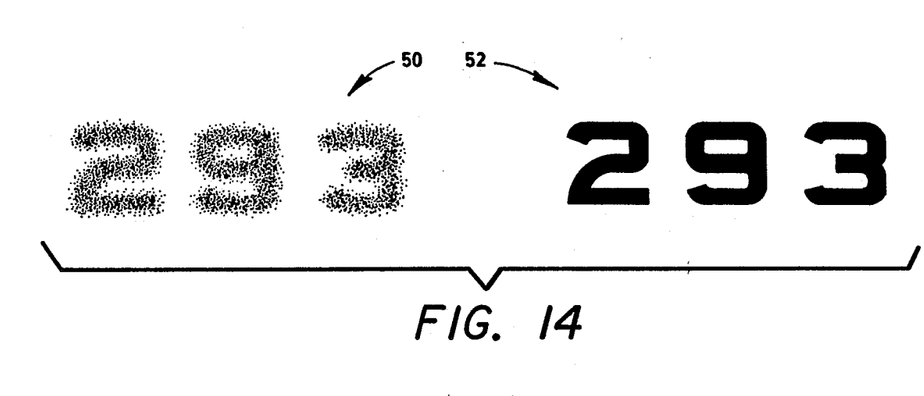
FIG. 14 shows the results of a test of the masked IOL of the present invention for astigmatism.

The results of the model eye testing are shown in FIGS. 12 through 14. In FIG. 12, the model eye was compared using a standard IOL and a masked IOL in accordance with the present invention as represented by 38 of FIG. 11. The model eye was set up to look at an object at a reading distance through an average size pupil (3.4 mm). The masked IOL, as shown in FIG. 12, produces a clearer image 40 than the image 42 produced by a standard IOL. The masked IOL has overcome the large refractive error and has brought the near image 40 into sharp focus.

In FIG. 13, the model masked IOL in accordance with the present invention as represented by 38 of FIG. 11 was tested to determine its performance with different sized pupils. With an average sized pupil, diameter x of 3.4 mm as shown in FIG. 13, the quality of the image 44 is very good, as would be expected from the pinhole 15. As the pupil 37 dilates to a diameter x' of 4.5 mm and then to a diameter x" of 5.6 mm, and more light is admitted to the eye, the images 46, 48 achieved degrade although not significantly.

In FIG. 14, it is shown that the masked IOL also corrects for astigmatism. Cataract extraction introduces a certain amount of post-operative astigmatism in most patients and refractive correction is often needed. On the left of FIG. 14 is an image 50 produced by an astigmatism of +1.5 diopters. This degree of astigmatism is not uncommon on post-operative cataract patients. On the right is an image 52 of the same astigmatism, as seen through the masked IOL 38. As can be seen from FIG. 14, the image 52 is much clearer.

Figure 15A:
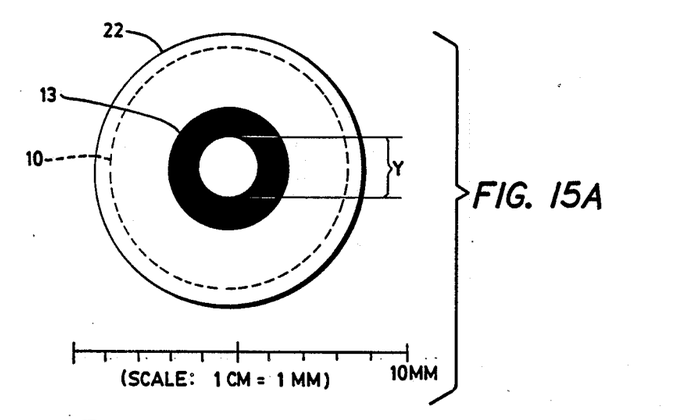
FIGS. 15A, 15B, and 15C show the masked IOL of the present invention and what happens when the IOL becomes decentered.
Figure 15B:
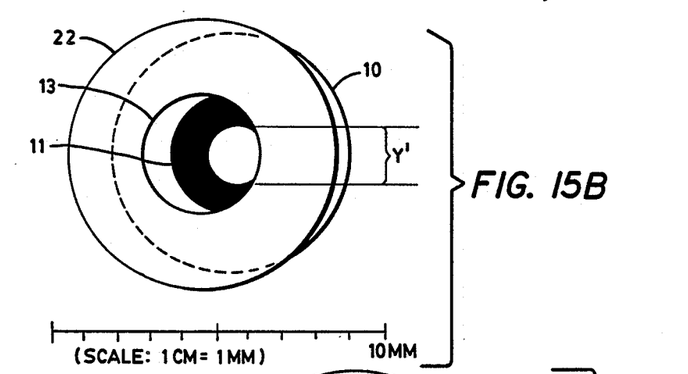
Figure 15C:
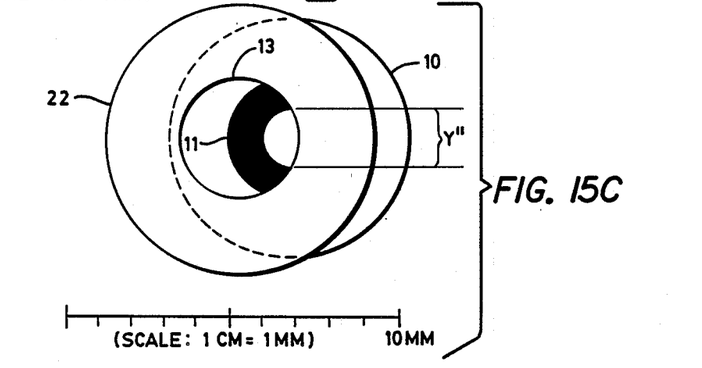

Decentration of the IOL is a problem in post-operative cataract patients. Recent epidemiological data has shown that 84 percent of all IOLs show decentration of less than 1.1 mm. Larger decentrations are a rare event. The range of decentration in 99.5 percent of all cases of IOLs goes from 0.1 mm to 1.9 mm. In other words, fewer than one-half of one percent of the IOLs have decentrations more severe than 1.9 mm. Decentration is especially a problem for known bifocal type IOLs. Shown in FIG. 15A is a masked IOL 10 centered within the pupil 13. In this case, there is obviously no problem because the full aperture, a 2 mm diameter y in this example, is exposed. In FIG. 15B there is shown a 1.1 mm decentration. This decentration does not effect patient vision with the masked IOL design. The aperture area y' is 2 mm by 1.6 mm. Even in FIG. 15C, the pinhole is perfectly functional with a 1.9 mm decentration. The aperture area y" is 1.8 mm×1.0 mm. Since only one-half of one percent of the IOLs would have decentrations greater than that shown in FIG. 15C, the masked IOL of the present invention would be functional 99.5 percent of the time.

Figure 16A:
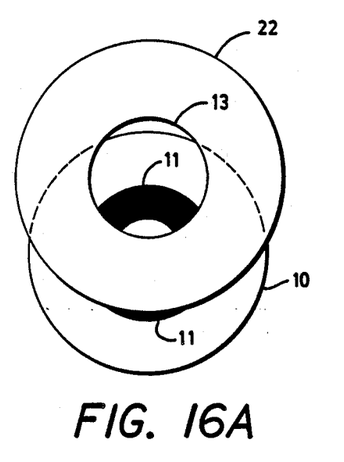
FIGS. 16A, 16B, and 16C show the procedure for correcting extreme decentration of the masked IOL of the present invention.
Figure 16B:
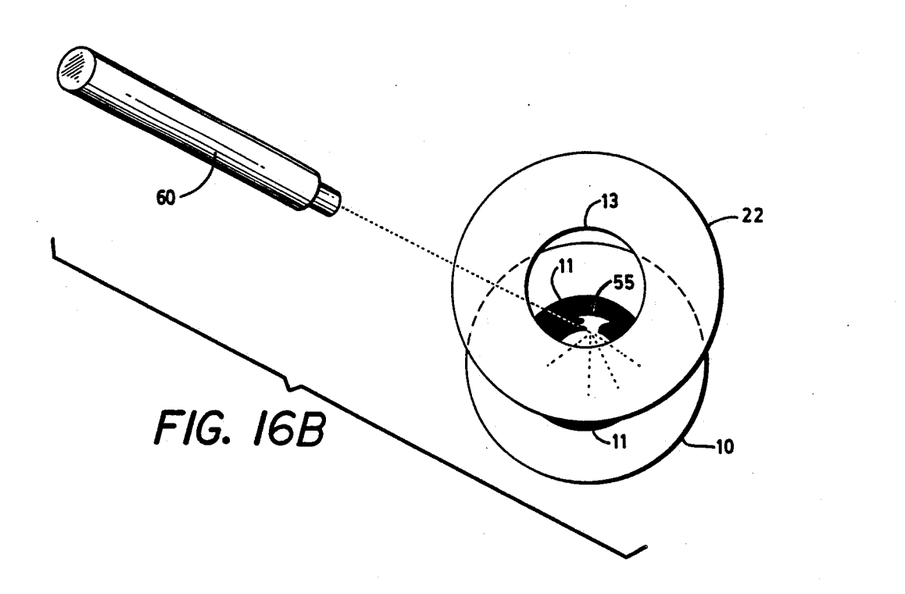
Figure 16C:
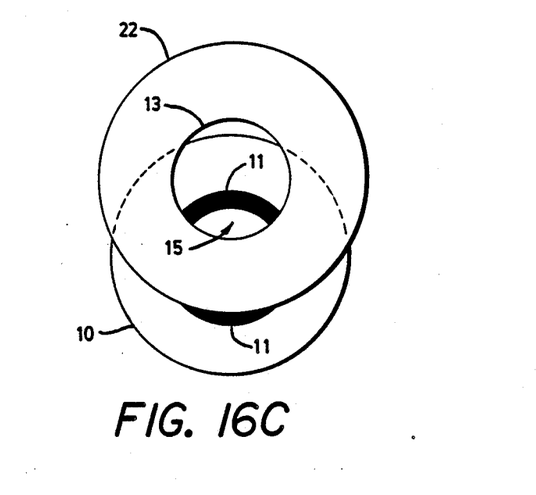

However, in decentrations of more than 1.9 mm, standard IOLs are often removed surgically. The masked pinhole allows one to solve even such a large decentration without surgery. In FIG. 16A, a decentration of 2.3 mm, which is extremely rare, occurring in less than 0.1 percent of patients, is shown. In FIG. 16B, the opaque mask 11 has a preformed cut 55 that aids the ophthalmologist in creating a larger opening. As shown in FIGS. 16B and 16C, it may be possible to disintegrate the edge of the mask along the preformed cut 55 with a Nd:YAG laser 60. The masked IOL has a new larger aperture 15 which functions as a pinhole.

Figure 17:
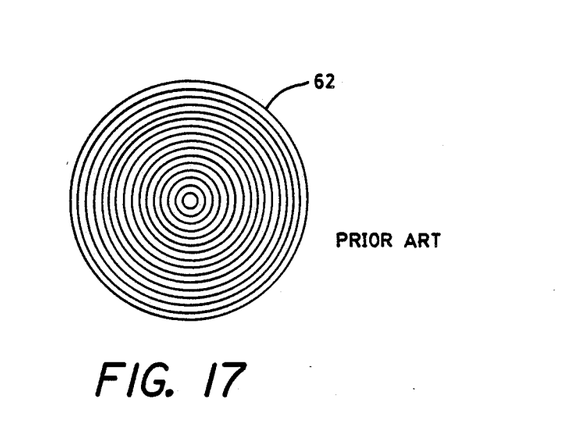
FIG. 17 shows a diffractive IOL of the prior art.

Table 2 below shows a comparison of a new diffractive IOL 62, shown in FIG. 17, and the masked IOL 10 of FIG. 6 of the present invention.

TABLE 2

|  | Masked IOL | Diffractive IOL |
| --- | --- | --- |
| Corrects for Astigmatism? | YES | NO |
| Exact Lens Power Critical? | NO | YES |
| # of Dioptric Powers | CONTINUOUS | 2 |
| Decreases Contrast | NO | YES |
| Sensitive to Displacement | NO | NO |
| Night Glare a Problem? | NO | YES |

There are listed six bases of comparison. The masked IOL 10 corrects for astigmatism while the diffractive IOL 62 does not. The diffractive IOL 62 requires the production of the exact lens power needed post-operatively which is critical to the functioning of the lens 62 while such is not the case for the masked IOL 10. The number of dioptic powers is continuous in the masked IOL 10 allowing vision at all distances while the diffractive IOL 62 has only two dioptic powers. The diffractive IOL 62 decreases contrast which is not the case with the masked IOL 10. The masked IOL 10 is insensitive to displacement as is the diffractive IOL 62. Finally, the diffractive IOL 62 has a problem with night glare (because of light scattering from the rings) while such is not the case with the masked IOL 10.

In the preferred embodiment of the intraocular lens of the present invention, the optic is made of a material such as polymethylmethacrylate (PMMA). This material is commonly used for making intraocular lenses. The fabrication of the intraocular lens, per se, forms no part of the present invention. The mask of the present invention is made of an opaque material, such as suture dye. The suture dye is applied to the PMMA to produce an opaque pattern on the IOL of the present invention. The dye may be applied to either the back or front surface of the lens or both. It may also lie within the lens. The important point is that it be applied in such a way that that part of the IOL which is to be masked is opaque. In a preferred embodiment, the dye will be applied to the back surface so that it can be removed with a Nd:YAG laser in the case of decentration as described above.

While the foregoing invention has been described with reference to its preferred embodiments, it should not be limited to such embodiments since various alterations and modifications will occur to those skilled in the art. For example, the mask of the present invention can be a different shape than is shown in the figures. All such variations and modifications are intended to fall within the scope of the appended claims.

What is claimed is:

1. An intraocular lens comprising:
   a transparent lens body adapted to be implanted in the human eye for focusing light rays on the retina of the eye and having means for attachment to the interior of the eye,
   said lens body having an opaque mask involving only a part of the lens body such that a small aperture results near the optical center of the lens body when the lens is implanted in the eye and the pupil of the eye is constricted such that when the pupil of the eye is constricted the mask on the lens body together with the constricted pupil only allows light to reach the retina through the small aperture to create a sharp image in bright light, said opaque mask also being configured so that a larger light path through the lens body is defined by the mask such that when the pupil is dilated in dim light, a greater percentage of the transparent portion of the lens is exposed to light.

2. The intraocular lens according to claim 1 wherein said small aperture is approximately 2.0 mm in diameter.

3. The intraocular lens according to claim 1 wherein the lens is made of polymethylmethacrylate.

4. An intraocular lens comprising:
a transparent lens body adapted to be implanted in the human eye for focusing light rays on the retina of the eye and having means for attachment to the interior of the eye,
said lens body having an opaque mask involving only a part of the lens body, said opaque mask involving the upper half of the lens body except for a small portion near the optical center of the lens so that a small aperture results near the optical center of the lens body when the lens is implanted and the pupil of the eye is constricted such that when the pupil of the eye is constricted the mask on the lens body together with the constricted pupil only allows light to reach the retina through the small aperture to create a sharp image in bright light, and said opaque mask also extending into the lower half of the lens body in two symmetrical approximate half circles about the center of the lens body so that a large light path is defined by the mask such that when the pupil of the eye is dilated in dim light, a greater percentage of the transparent portion of the lens is exposed to light.

5. The intraocular lens according to claim 4 wherein said small aperture is approximately 1-3 mm in diameter.

6. The intraocular lens according to claim 4 wherein said lens body is made of polymethylmethacrylate.

7. An intraocular lens comprising:
a transparent lens body adapted to be implanted in the human eye for focusing light on the retina of the eye and having means for attaching to the interior of the eye,
said lens body having an annular opaque mask surrounding a central portion of said lens body such that the annular opaque mask defines a small circular aperture in the lens body which allows light to reach the retina such that when the pupil of the eye is constricted the mask on the lens body together with the constricted pupil only allows light to reach the retina through the small aperture to create a sharp image in bright light, said annular opaque mask also defining a larger exterior annular path for light to reach the retina such that when the pupil of the eye is dilated in dim light, a greater percentage of the transparent portion of the lens is exposed to light.

8. The intraocular lens according to claim 7, wherein said small circular aperture is approximately 2 mm in diameter.

9. The intraocular lens according to claim 7, wherein said annular opaque mask is approximately 1.5 mm in width.

10. The intraocular lens according to claim 7, wherein the lens body is made of polymethylmethacrylate.

11. The intraocular lens according to claim 7, wherein the annular opaque mask can be removed by a Nd:YAG laser.

12. The intraocular lens according to claim 7, wherein said central portion of said lens body within the area defined by the inner edge of said annular opaque mask has an additional focusing power of approximately 1.5 diopters beyond that needed for clear distance vision.

13. A method for treating a cataract patient comprising:
removing a dysfunctional lens from an eye of the patient; and
implanting an intraocular lens in the eye of the patient wherein the implanted intraocular lens includes a lens body having an opaque mask involving only a part of the lens body such that a small aperture results near the optical center of the lens body when the lens is implanted in the eye and the pupil of the eye is constricted such that when the pupil of the eye is constricted the mask on the lens body together with the constricted pupil only allows light to reach the retina through the small aperture to create a sharp image in bright light, said opaque mask also being configured so that a larger light path through the lens body is defined by the mask such that when the pupil is dilated in dim light, a greater percentage of the transparent portion of the lens is exposed to light.

14. A method for treating a patient with cataracts comprising:
removing a dysfunctional lens from an eye of the patient; and
implanting an intraocular lens in the eye of the patient wherein the implanted intraocular lens includes a lens body having an opaque mask involving only a part of the lens body, said opaque mask involving the upper half of the lens body except for a small portion near the optical center of the lens so that a small aperture results near the optical center of the lens body when the lens is implanted and the pupil of the eye is constricted such that when the pupil of the eye is constricted the mask o the lens body together with the constricted pupil only allows light to reach the retina through the small aperture to create a sharp image in bright light, and said opaque mask also extending into the lower half of the lens body in two symmetrical approximate half circles about the center of the lens body so that a large light path is defined by the mask such that when the pupil of the eye is dilated in dim light, a greater percentage of the transparent portion of the lens is exposed to light.

15. A method for treating a patient with cataracts comprising:
removing a dysfunctional lens from an eye of the patient; and
implanting an intraocular lens in the eye of the patient wherein the implanted intraocular lens includes a lens body having an annular opaque mask surrounding a central portion of said lens body such that the annular opaque mask defines a small circular aperture in the lens body which allows light to reach the retina such that when the pupil of the eye is constricted the mask on the lens body together with the constricted pupil only allows light to reach the retina through the small aperture to create a sharp image in bright light, said annular opaque mask also defining a larger exterior annular path for light to reach the retina so that when the pupil of the eye is dilated in dim light, a greater percentage of the transparent portion of the lens is exposed to light.

* * * * *